United States Patent [19]

Lionetti et al.

[11] 4,004,975

[45] Jan. 25, 1977

[54] METHOD OF ISOLATING AND CRYOPRESERVING HUMAN WHITE CELLS FROM WHOLE BLOOD

[75] Inventors: Fabian J. Lionetti, Milton; Stephen M. Hunt, Allston, both of Mass.

[73] Assignee: The United States of America as represented by the Secretary of the Navy, Washington, D.C.

[22] Filed: Dec. 30, 1975

[21] Appl. No.: 645,161

[52] U.S. Cl. .................................. 195/1.8; 62/62; 424/101

[51] Int. Cl.² .................... C12K 9/00; F25D 25/00; A61K 35/14

[58] Field of Search .................... 424/101; 195/1.8; 62/62

[56] References Cited

UNITED STATES PATENTS

| | | | |
|---|---|---|---|
| 2,910,406 | 10/1959 | Novak | 424/101 |
| 3,170,838 | 2/1965 | Archer | 424/101 |
| 3,328,255 | 6/1967 | Ilg | 424/101 |

Primary Examiner—Sam Rosen
Attorney, Agent, or Firm—R. S. Sciascia; L. I. Shrago; C. E. Vautrain, Jr.

[57] ABSTRACT

A method of salvaging granulocytes, or white cells, from buffy coat of centrifuged whole blood is provided. The sequence of operations leading to the separation red cells, white cells, platelets and plasma is presented in a flow diagram of a bag system for the cryopreservation of leukocytes, with freezing of the white cells accomplished by the introduction of a combination of hydroxyethyl starch (HES), which functions as both a sedimenting agent and a cryoprotective agent, and dimethylsulfoxide (DMSO), a cryoprotective agent. A preferred combination is 4% HES with 5% DMSO. White cell separation is interfaced with collection methods for plasma and platelets so as to conserve all major cell types.

10 Claims, 6 Drawing Figures

METHOD OF ISOLATING AND CRYOPRESERVING HUMAN WHITE CELLS FROM WHOLE BLOOD

The present invention concerns the preservation of granulocytes and, more particularly, the freezing of granulocytes of peripheral blood and the production of a substantial yield of thawed viable cells as determined by in vitro characteristics.

A method of preserving granulocytes has long been sought and is clinically necessary, e.g. in order to combat severe infections associated with severe granulocytopenia. The numbers of cells required for a significant elevation of circulating leukocytes is about 5-10 times the number available in the usual pint whole blood collection where the standard dose is $10^{10}$ PMNs per $m^2$ of body surface. Presently, this magnitude of cells can only be obtained from single donors subjected to filtration leukophoresis or continuous flow centrifugation methods. The in vitro half-life of neutrophils at 4° C is about two days. Although approximately one-half of the leukocytes from whole blood collected in blood banks is readily obtained by centrifugation and sedimentation, nearly all of the leukocytes from millions of blood collections are presently wasted.

Differential rates of sedimentation of the cellular components of blood have been extensively applied to the separation of granulocytes from the time it was demonstrated that the rate of cell sedimentation was determined by the size and character of erythrocyte rouleaux. It has been shown that leukocytes from whole blood can be obtained for in vitro study by acceleration of erythrocyte sedimentation with fibrinogen. The red cells were aggregated by rouleaux formation and sedimented rapidly while the white cells remained in suspension. Isolation of human leukocytes by sedimentation of whole blood with a variety of rouleaux-promoting agents has been studied and a method employing an 0.8% dextran solution has been suggested. In addition to dextran, other agents used include phytohemagglutinin, polyvinylpyrrolidone, fibrinogen, gelatin and sugar polymers.

Hydroxyethyl starch (HES) has been used to isolate leukocytes and dimethylsulfoxide (DMSO) has found extensive experimental use as an intracellular cryoprotective agent particularly of nucleated cells due to its high rate and universality of cellular penetration. No material or combination of materials has yet, however, been identified which would demonstrate the feasibility of freezing granulocytes of peripheral blood and producing a good yield of thawed viable cells as judged by in vitro characteristics. From banked blood, the utility of such a freezing and thawing system is presently limited, although the potential exists for salvaging about half of the white cells from more than 20 million blood collections in the United States every year. The yields from single units are too low for transfusions into granulocytopenic patients, and pooling of white cells from multiple units is impractical due to immunological differences. The major losses occur in the isolation procedure as nearly half of the cells are lost in isolating buffy coat, and almost half of the remainder during sedimentation. Therefore, despite the virtue of simplicity, much improvement in yields prior to freezing should be sought. A major limitation is the need to handle whole blood in a manner compatible with the isolation of other components, e.g. plasma and platelets. When whole blood is centrifuged under conditions optimal for platelet isolation, 1000g for 3 min., the yield of leukocytes in buffy coat is of necessity reduced. In the sedimentation procedure with HES, small lymphocytes and erythrocytes sediment together so that the leukocytes in the supernatant are depleted of most of the lymphocytes. Whereas this is advantageous in granulocyte isolation and preservation, it is wasteful of lymphocytes.

The present invention advances the state of the art of granulocyte isolation and preservation by defining a combination of HES with DMSO which produces an acceptable level of preservation of granulocytes as determined by an assessment of several physiological characteristics of the preserved and thawed granulocytes.

Accordingly, it is an object of the present invention to provide a method compatible with component blood banking for the harvesting and freezing of buffy coat leukocytes.

Another object of this invention is to provide a method of isolating mixed leukocytes from human whole blood and to preserve them by freezing.

A further object of this invention is to provide a method of freezing granulocytes of peripheral blood and a method of determining the feasibility of thawed cells by tests involving cell morphology and their ability to inhibit growth of Escherichia (E.) coli.

Other objects, advantages and novel features of the invention will become apparent from the following detailed description thereof when considered in conjunction with the accompanying drawings in which like numerals represent like parts throughout and wherein.

In general, the invention concerns a method of harvesting and freezing buffy coat leukocytes which is compatible with component blood banking and which comprises the sedimentation of buffy coat leukocytes with HES to aggregate erythrocytes and concentrate the leukocytes, and the cryopreservation thereof by cooling the concentrate to −80° C in the presence of residual HES and 5% DMSO.

HES is very useful in the methods of the present invention since it promotes red cell aggregation and, when a high ratio of red cells to white cells exists as in aspirated marrow, the concentration of myeloid cells by differential sedimentation of erythroid cells leaving an enriched leukocyte concentration containing residual HES. The granulocyte concentrate, while contained in the plastic bag in which the sedimentation took place, is placed in a −80° C freezer to freeze at a slow rate to produce a substantial yield of biologically active postthawed cells.

Leukocytes, i.e. white cells, comprise a numerically small fraction, 0.002, of the blood cells in human whole blood. They are obtainable in concentrated suspensions by means of selected sedimentation under gravitational force. Small numbers, i.e. $1 \times 10^6 - 10 \times 10^6$, have been frozen for limited periods, and the thawed cells have been shown to retain biochemical and morphological characteristics suggesting retention of physiological competence after preservation. Sedimentation is enhanced by agents which promote rouleaux formation, i.e. aggregates, of red cells. These settle out leaving white cells concentrated in suspension. Fibrinogen has been used, but at the high concentrations required for optimum sedimentation of red cells the viability of white cells decreases.

Dextran, fibrinogen and phytohemagglutinin have been used as a test tube technique in which, however, the agents are not approved for human use. Other compounds such as polyvinylpyrrolidone and gelatin also are not approved for human use. The agent used in the present invention, HES, has been used for this purpose, is FDA approved, and is undergoing clinical trials as an additive to blood to enhance the separation of white cells in centrifugation techniques. Other means to isolate white cells are by adsorption onto nylon, electronic separation, and selective lysis of red cells. White cells have been frozen with DMSO and with glycerol, with relatively low yields of functional white cells being derived.

Figure 1:
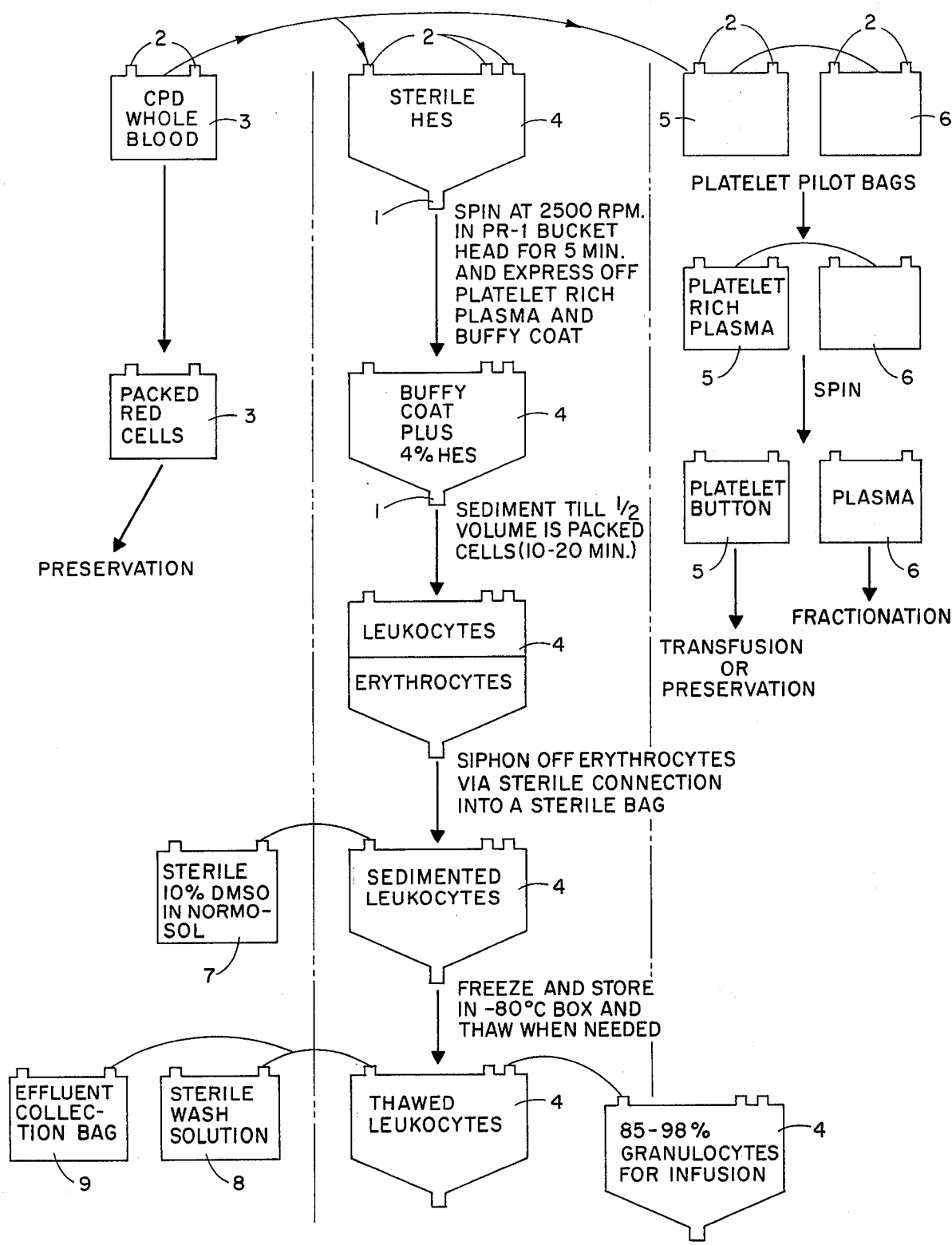
FIG. 1 is a flow diagram of the sequence of operations for separating red cells, white cells, platelets and plasma.

FIG. 1 presents one embodiment of the present invention that features a bag method of isolating granulocytes (leukocytes) which lends itself to sterile handling and which is compatible with the isolating of all of the cellular elements of the blood. In FIG. 1, a preferred bag system is set forth for the cryopreservation of leukocytes. The figure shows bags which are numbered and/or captioned for identification and are provided with tubes 1 and ports 2, respectively. A blood collection bag is indicated at 3 and is attached serially to a white cell sedimentation and freezing bag indicated at 4, and to platelet and plasma bags indicated at 5 and 6, respectively. The flow diagram of FIG. 1 also includes the sequence of operations leading to the separation of red cells, white cells, platelets and plasma, and the freezing, thawing and washing of white cells. The details of the methods of the present invention, the materials used therein, and an analysis of the results achieved are set forth infra. It will be appreciated that test tubes may be replaced by plastic bags in the performance of these methods. Freezing of the white cells is accomplished with a combination of HES, which functions as both a sedimenting and cryoprotective agent, and DMSO, a cryoprotective agent.

Isolation of Buffy Coat Leukocytes

Units of whole blood, 450 ml, anticoagulated with citrate-phosphate-dextrose (CPD), 63.0 ml containing 206 mg citric acid, 1.66 g sodium citrate, 140 mg of sodium biphosphate and 1.6 g dextrose, were obtained from male donors. The blood was centrifuged in collection bags, Fenwal quadruple blood pack JA-45 Fenwal Laboratories, Division of Travenol Laboratories, Morton Grove, IL 60053, for 450 ml whole blood, in an International PR-1 refrigerated centrifuge, International Equipment Co., Boston, MA, for 3 min. at 1000g. The platelet rich plasma was expressed and the buffy coat plus 50 ml, total 90, of topmost red cells extracted either into a satellite bag containing HES or into a beaker for routine testing.

Hydroxyethyl Starch

The HES, 40% weight/volume, McGraw Laboratories, Glendale, CA, Lot No. P1-P005, inherent viscosity 0.15 ml/g, degree of substitution 0.75, av MW 150,000, in 0.15 m NaCl was prepared by dissolving 42.7 g powder in 70 ml distilled water and adjusting the volume to 100 ml. It was routinely made this way and used as a stock solution of 40% w/v. The concentration of HES was verified by polarimetry using a specific rotation of HES of 182° as suggested by the manufacturer. From these, dilutions ranging from 10 to 16% were made with Normosol-R, pH 7.4, an isotonic solution of salts containing 148 mequiv per liter each of cations, $Na^+$ 140, $K^+$ 5 and $Mg^{2+}$ 3, and anions, chloride 98, acetate 27 and gluconate 23, supplied by Abbott Laboratories, North Chicago, IL.

Sedimentation of Red Cells from Buffy Coat

As harvested, buffy coat cells had hematocrits of approximately 0.39–0.50. These were admixed with predetermined volumes of concentrated HES so that sedimentation of red cells in the cell mixture could be carried out at a hematocrit of 0.30 at a final concentration of 4% HES. For instance, after removal of a few ml for testing if the buffy coat volume was 78 ml, a volume of 53 ml of 10% HES would be required to produce a final concentration of 4% and a hematocrit of from 0.20 to 0.30. This was done at 22° C by addition of starch solution to the beaker. After mixing, the cells-starch mixture was sedimented in 30.0 ml plastic syringes standing upright on the plungers. After 55 min. the leukocyte-enriched supernatant to the red cell interface was pushed vertically out of the syringes through curved needles. Most of the data recorded herein were acquired with this procedure.

Sedimentation in Plastic Bags

Sedimentation was undertaken in plasma transfer packs, Fenwal TA-2, 300 ml, attached to the collecting unit using the same volume of cells, dilutions and starch concentrations. Sedimentation was for 20 min. at 22° C. Leukocyte enriched supernatants, about 50–60 ml, were expressed into small platelet preservation bags, Hemoflex, style 1000-2, Union Carbide Co., Chicago, IL. To these DMSO, 10%, was added at the slow rate of 2.0 ml/min. through a connecting port to a final concentration of 5% w/v.

Cryopreservation of Concentrated Granulocytes

Two-milliliter aliquots, approximately $2 \times 10^7$ cells, of leukocytes isolated by sedimentation were placed in polyethylene plastic tubes, $17 \times 100$ mm, and frozen at 2° C/min. to −80° C. They were stored at −80° C for periods up to 3 months in a Harris −80° C mechanical refrigerator, cascade type Model 10L210, Harris Manufacturing Co., Cambridge, MA. The suspensions from the sedimentation procedure, about 55 ml containing $6 \times 10^8$ white cells, were frozen by placing the bags flat in the freezer at −80° C. Residual HES remaining after sedimentation was the cryoprotective agent for half the units studied while the remainder contained 5% DMSO in addition as described above. Analysis by polarimetry and anthrone of HES in supernatants from centrifuged samples of white cell suspensions showed no changes in HES concentration as a result of the sedimentation procedure.

Thawing

Tubes of granulocytes were thawed at 37° C in a water bath with shaking, 160 cycles/min., for 3–5 min. until cool to the touch. Plastic bags were placed in a metal holder and thawed similarly for 1–2 min. depending on the volume frozen. Washing of postthawed granulocytes containing DMSO was effected by adding Normosol-R, adjusting to pH 7.4 containing CPD at a rate of 2.0 ml/min. until 5 volumes, 10 ml, were added. The tubes were gently mixed and centrifuged at 600g for 60 seconds. The supernatant layer, 8.0 ml, was removed by aspiration and the pellet of white cells resuspended in Normosol-R by gentle agitation. Granulocytes frozen in plastic bags after thawing were washed similarly as were those frozen only with residual HES and no DMSO.

Testing Procedures

Leukocytes from whole blood, and prefrozen and postthawed granulocyte concentrates, were examined in Wright's stained smears. Differential counts of cell types were obtained at 1000 magnifications. Granulocyte concentrates were also tested for myeloperoxidase activity in air dried smears and trypan blue exclusion in fresh wet preparations. Cell size distributions of prefrozen and thawed granulocytes were made with a multichannel cell-size analyzer such as the Coulter Particle Counter manufactured by Coulter Electronics, Inc., Hialeah, Fla. 33104, which is adaptable for submicron and micron particle analysis. Size distributions were also used to indicate cellular integrity from the areas under the representative peaks and from the heights and widths of the white cell populations in the distributions. This technique is described in an article entitled Control of Cell Size in the cryopreservation of Mouse Marrow by F. J. Lionetti et al in Cryobiology, Vol. 9 pp. 488–495, 1972.

Tests of Inhibition of Bacterial Growth by Granulocytes

E. coli, ATCC 2355, were inoculated from Difco Bactrol discs, Difco Laboratories, Detroit, MI, the night prior to testing into a medium of TC 199, a tissue culture medium specially prepared for growing cells, pH adjusted to 7.2 with $NaHCO_3$, Microbiological Associates, Bethesda, MD, and incubated at 37° C with orbital shaking, 100 rotations/min. 1 cm radius. On the day of testing, fresh particle-free 10% TC 199 solution in Normosol, pH 7.2, was prepared. Fifty milliliters were placed in a polycarbonate beaker to which an inoculum of E. coli from the overnight culture was added.

The assays of bacterial growth were made electronically with the multichannel cell-size analyzer. To include the range of cell diameters, appropriate window settings were used to count E. coli and white cells, E. coli 0.2–2.0 μm, white cells 4.0–14 μm. Standard latex particles were used to relate channel numbers to cell diameters and to standardize the instrument for daily variations in sensitivity. Ten milliliters of cell suspensions were usually placed in the instrument of which 0.05 ml was sampled and counted. By plotting electronically the frequencies of occurrence of signals for each channel versus the cumulative number of channels, the data is obtained as a distribution of cell sizes. White cell and bacterial counts were obtained by integrating areas under the size distribution curves.

To measure the effects of frozen granulocytes on growth, E. coli were diluted with 10% TC in Normosol to a count of 2,000 per 0.05 ml. A 10-ml culture was maintained at 37° C with shaking and counts made periodically on 0.05-ml aliquots until exponential growth was established. It was then diluted again with medium to a count range of 2,000–3,000 per 0.05 ml and reincubated until exponential growth was reestablished. Thawed granulocytes, 0.5 ml, isolated by the sedimentation procedure with HES were diluted to 15.0 ml with Normosol. They were then counted electronically by integration of the area under the size distribution curve, diluted to give the desired concentration and added to proliferating E. coli. The mixture was incubated with shaking at 37° C and 0.05-ml aliquots withdrawn periodically and bacteria counted for several hours. A group of control experiments indicated that growth was not inhibited by Normosol, DMSO or supernatants from centrifuged fresh and frozen-thawed white cells after mixing with E. coli in exponential growth.

Results

Figure 2:
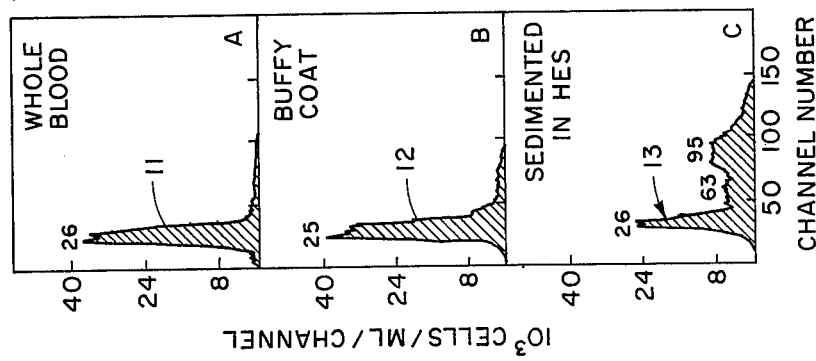
FIG. 2 is a series of graphs showing the separation of granulocytes from whole blood by sedimentation with HES.

The separation of leukocytes from whole blood by sedimentation in 4% HES is depicted in FIG. 2. Whole blood is centrifuged and buffy coat obtained and sedimented with HES as described supra. Curves 11, 12 and 13 are size distributions of cells of whole blood, buffy coat and granulocyte concentrate, respectively. Cells are distributed according to size, abscissa, and frequency of occurrence, ordinate. Curve 11 for whole blood is the usual well-defined peak corresponding to the red cell population obscuring the other cells present. In this blood sample the ratio of red to white cells was 900:1. The buffy coat obtained from whole unit centrifugation is represented in curve 12. The distribution of cells in the buffy coat was similar to that of whole blood, except that there are larger cells present as indicated by the higher frequency of cells between channels 40 and 100. The ratio of red blood cells to white blood cells in the buffy coat was 140:1, representing a 6-fold concentration of white cells. The curve obtained by electronic monitoring of the granulocyte concentrate produced from sedimented buffy coat is shown at 13. Three well-defined peaks were observed. The removal of the majority of red cells by HES sedimentation revealed the size distribution of two large major cell populations. The first peak, channel 26, corresponded to red cell and small lymphocytes, the middle peak, channel 63, represented larger lymphocytes, and the third peak, channel 95, consisted of granulocytes. The numbers on the peaks correspond to the median channel number obtained directly from the particle size analyzer.

Figure 3:
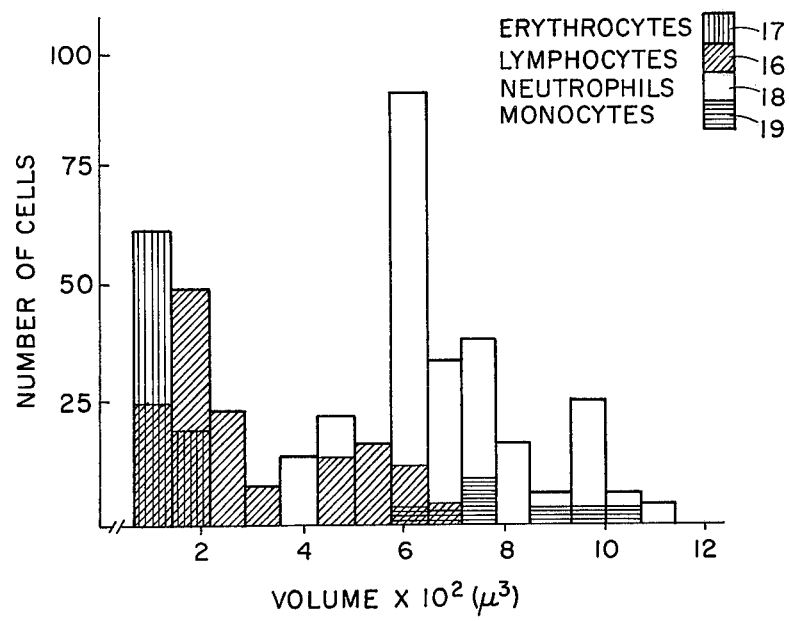
FIG. 3 is a graphical illustration of the distribution of cell types in sedimented buffy coat.

Smears were made, air dried, and the slides stained with Wright's stain. Cell types were identified microscopically from the hanging drop preparations and diameters ranging from 5.0 to 13.5 microns were measured for 500 cells, using an image-splitting eyepiece. The distribution of the three major cell types according to histological sizing is shown in the bar graph of FIG. 3 which concerns microscopic identification of cell types in sedimented buffy coat magnified 900X. Volumes were computed from measured diameters using the formula $V = 4/3 \pi (D/2)^3$, assuming all cells were spherical. Visual sizing of the red cells microscopically corresponded to the narrow diameter limits found with the electronic measurements of whole blood and buffy coat. The lymphocytes, indicated at 16, fell into two groups. Smaller lymphocytes occurred in the same range as erythrocytes, indicated at 17, and were seen to make up nearly 50% of the first peak of the distribution curve measured electronically of the HES sedimented supernatant, curve 13 of FIG. 2. The larger lymphocytes were smaller than the neutrophils, indicated at 18, and showed the greatest variation from sample to sample. Correspondingly, a middle lymphocyte peak on the particle-size analyzer was occasionally obscured by red cells or granulocytes of the same size. Neutrophils were the predominant cell type of the leukocyte population and were the major constituent of cells with diameters larger than 9.5 $\mu$m. Monocytes, indicated at 19, made up less than 4% of the total cells counted and their presence or absence did not appreciably affect the cell distribution curve. Eosinophils, basophils, and plasma cells representing less than 1% of the total cell population were not included. The shape of the distribution curves for cells sized microscopically, FIG. 3, corresponded with the shape of the cell distributions measured electronically, curve 13 of FIG. 2.

The recovery based on cell count of white cells separated from 10 units of whole blood is summarized in Table 1, infra.

TABLE 1

WHITE CELLS SEPARATED FROM WHOLE BLOOD[a]

| Cell type | Whole blood (count/unit) | Buffy coat (count/total vol) | Granulocyte concentrate (count/total vol) |
|---|---|---|---|
| RBC | $(2.1\pm0.2) \times 10^{15}$ | $4.2 \times 10^{11}$ | $(5.1\pm2.2) \times 10^9$ |
| WBC | $(2.7\pm0.8) \times 10^9$ | $1.6 \times 10^9$ | $(6.6\pm0.3) \times 10^8$ |
| RBC/WBC | 830±230:1 | 290±135:1 | 9.3±6.6:1 |
| Polys/lymphs | 65:30 | 55:45 | 85:15 |
| White cells Recovered % of whole blood | 100 | 60±9.7 | 26±9.9[b] |

[a] Average + SD, $\eta = 10$.
[b] The value of 26±9.9 was obtained by multiplying the yields from buffy coat (60±9.7 and granulocyte concentrate (43±14).

The average number of white and red cells, the ratio of polymorphonuclear leukocytes to lymphocytes, and the percentage recovered is tabulated. It is seen that harvesting of buffy coat leukocytes by centrifugation of whole blood units in their collection bags yielded 60 ± 9.7% of available cells with a disproportionate loss of the smaller cells. Sedimentation with HES yielded 42 ± 14% of available leukocytes of which the greatest number were granulocytes; poly/lymphs = 85:15. In this procedure, lymphocytes evidently sedimented with erythrocytes and were separated during extrusion of the concentrate. The product of the above number, 60 × 43, yields 26% of the white cells of whole blood recovered in the sedimentation. Data later acquired with the sedimentation carried out in bags indicated a reasonable expectation of average yields in the 30–40% range.

Figure 4:
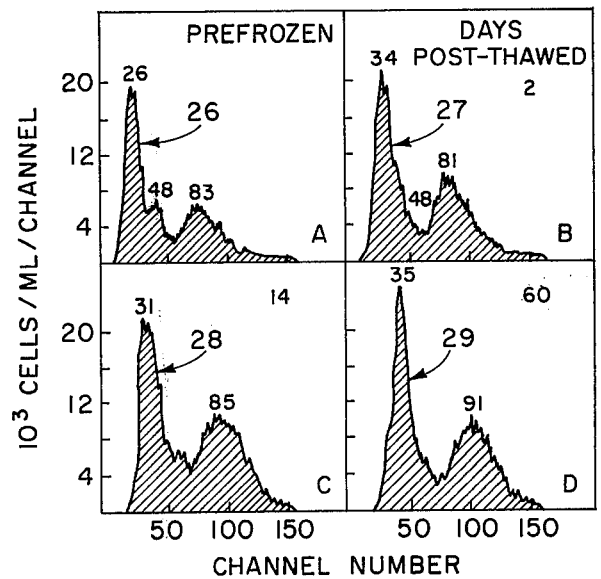
FIG. 4 is a series of graphs illustrating the size distribution of granulocytes preserved at −80° C.

Granulocyte concentrates to which DMSO was added and the cells frozen, thawed and washed as described above, were examined for cell recovery, morphological and membrane integrity, myeloperoxidase activity, trypan-blue exclusion and ability to inhibit growth of E. Coli. Screening of thawed cells by means of electronic cell sizing was used as a rapid means to estimate cell damage due to freezing and is shown in FIG. 4 which is a series of curves of size distribution of granulocytes preserved at −80° C. The abscissa numerals represent size distribution determined electronically from a unit of whole blood, sedimented as described, the leukocytes of which were frozen in 2.0-ml aliquots, approximately $2 \times 10^7$ cells in each. Curve 26 is the distribution of cells prefrozen, with channel numbers corresponding to the peaks, i.e. of median cell sizes, identified. Curves 27, 28 and 29 are from tubes thawed at 2, 14, and 60 days, respectively, with cryopreservatives HES and DMSO present. The distribution of cells prior to freezing, curve 26, indicated erythroid, lymphoid, and granulocyte peaks at channel numbers 26, 48 and 82. It is evident that the granulocytes tolerated freezing and thawing stresses as the profile of the biggest cells was relatively unchanged, curve 27, peak number 81, postthawed. The erythrocytes were enlarged in the thawed state as evident from a shift in red cell population to the right. This shift still remained relatively unchanged, peak number 48.

Of interest is the effect of storage time on the frozen granulocytes. The cell distribution of curves 28 and 29 suggests that granulocytes tolerated freezing and storage for 14 and 60 days by virtue of the symmetry of the distribution. A shift in maximum from peak channel number 85, curve 28, to 91, curve 29, indicates progressive swelling of granulocytes at −80° C, or more probably, inconsistencies in freezing and thawing rates in different tubes. A decrease in area of the granulocyte distribution and a shift to larger cells is compatible with swelling and lysis yielding cellular fragments below the present limits of resolution as indicated in the article in Cryobiology by F. J. Lionetti et al., supra.

Postthawed recovery and viability of preserved leukocytes was examined with phase and light microscopy. Cell morphology was observed directly after thawing and 1 hour later. Freezing leukocytes without cryopreservatives HES or DMSO produced few intact cells and these displayed no functional characteristics, such as membrane (dye exclusion) or granular (myeloperoxidase) functions. In well-preserved granulocytes, membranes, cytoplasm and nuclei in both phase contrast and Wright's stained smears were hard to distinguish from prefrozen cells. Characteristics of prefrozen and postthawed leukocytes are described in Table 2, infra. Leukocytes frozen with HES residual after sedimentation, and in combination with DMSO were counted differentially and stained histochemically for myeloperoxidase activity and with trypan-blue dye. Postthawed cells frozen with HES or HES plus DMSO were compared. No major effect on cell types was observed with both cryomethods, or with washed samples. After sedimentation, but before freezing, essentially no difference existed in the poly-to-lymph ratio as well.

TABLE 2

CHARACTERISTICS OF PREFROZEN AND POSTTHAWED LEUKOCYTES

| Conditions | Cryomethod av ± SD | | | | | | | |
|---|---|---|---|---|---|---|---|---|
| | HES | | HES Washed 1× | | HES + DMSO 4% 5% | | HES + DMSO Washed 1× | |
| Number of cells × 10⁷ (2.0-ml aliquots) | 2.3 ± 1.3 | | — | | 1.2 ± 0.6 | | — | |
| Cell types (%) | PF[a] | PT[a] | PF | PT | PF | PT | PF | PT |
| Polys | 82 | 78 | 84 | 80 | 72 | 73 | 83 | 81 |
| Lymphs | 16 | 21 | 16 | 18 | 27 | 26 | 17 | 17 |
| Others | 2 | 1 | 0 | 2 | 1 | 1 | 0 | 2 |
| Trypan excluded (%) | | | | | | | | |
| Prefrozen | 96 ± 3.5 | | 87 ± 15 | | 89 ± 11 | | 89 ± 6 | |
| Postthawed | 48 ± 16 | | 32 ± 10 | | 84 ± 11 | | 70 ± 9 | |
| Myeloperoxidase (%) | | | | | | | | |
| Prefrozen | 70 ± 15 | | 64 ± 20 | | 22 ± 31 | | 69 ± 26 | |
| Postthawed | 77 ± 11 | | 76 ± 14 | | 43 ± 31 | | 74 ± 24 | |
| Cell yield postthawed (%) | 99 ± 24 | | — | | 101 ± 22 | | — | |

[a]PF is prefrozen; PT is postthawed. Averages from six experiments for cell types. Trypan excluded and myeloperoxidase measurements are means ± SD of 10 experiments.

Prefrozen cells with HES exhibited the highest exclusion of trypan blue and greatest percentage of myeloperoxidase positive cells. The enzyme in thawed cells did not change appreciably, nor did washing affect it significantly. However, freezing reduced trypan exclusion by 50%, 40 ± 16, and washing after freezing even further, 32 ± 10. DMSO in combination with HES gave the overall highest myeloperoxidase activity after thawing and washing. The enzyme was apparently inhibited in the presence of DMSO as both prefrozen, 22 ± 31, and thawed 43 ± 31, values were very low. However, removal of DMSO by washing restored activity to the 70% level. Trypan exclusion, while somewhat less in the presence of DMSO than HES, was unaffected by washing prefrozen cells, but reduced to 70 ± 9% after thawing and washing. On the basis of data given in Table 2, the most effective system was HES + DMSO with a wash by dilution and centrifugation after thawing, to remove DMSO.

Figure 5:
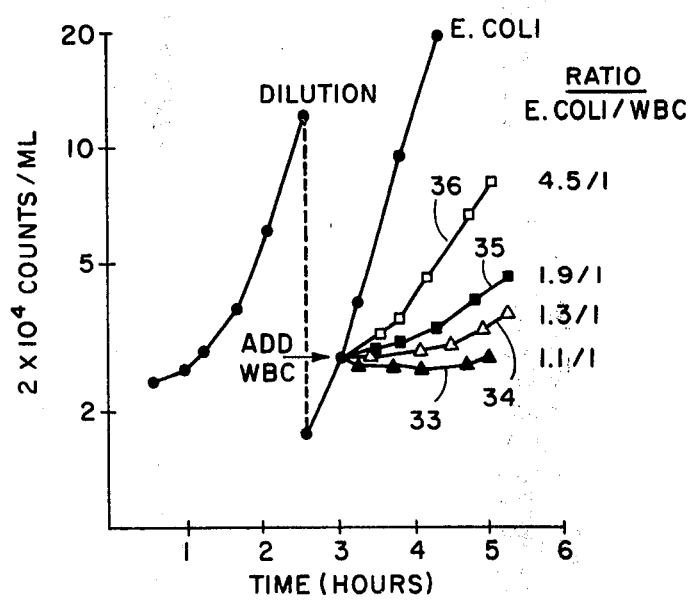
FIG. 5 is a graph showing the inhibition of growth of E. coli by white cells from sedimented buffy coat.

The ability of frozen and thawed granulocytes to inhibit growth of E. coli was tested by adding thawed leukocytes to actively growing cultures as described infra. Growth curves of E. coli for an experiment in which E. coli to white cell ratio varied from 4.5:1 to 1.1:1 are plotted in FIG. 5, which illustrates the inhibition of growth of E. coli by white cells from sedimented buffy coat. The points on the curves represent counts of E. coli cultured until in the log phase of growth as described infra. At the point marked "dilution" the culture was diluted to 40,000 cells/ml and growth reestablished in the curve marked "E. coli". Curves 33–36 represent growth curves in the presence of varying concentration of white cells. To these diluted cultures, white cells were added in ratios of 1:1 to 0.22 per bacterium. Counts were made with the multichannel cell analyzer. At the ratio of one bacterium per white cell, complete inhibition of growth, zero slope, was observed. As the number of E. coli per white cell increased, growth progressively increased until at a ratio of 4.5 E. coli to 1 white cell growth approached the normal rate. Photographs of white cells removed from the incubations with E. coli revealed ingested bacteria within the phagocytes, not shown.

Figure 6:
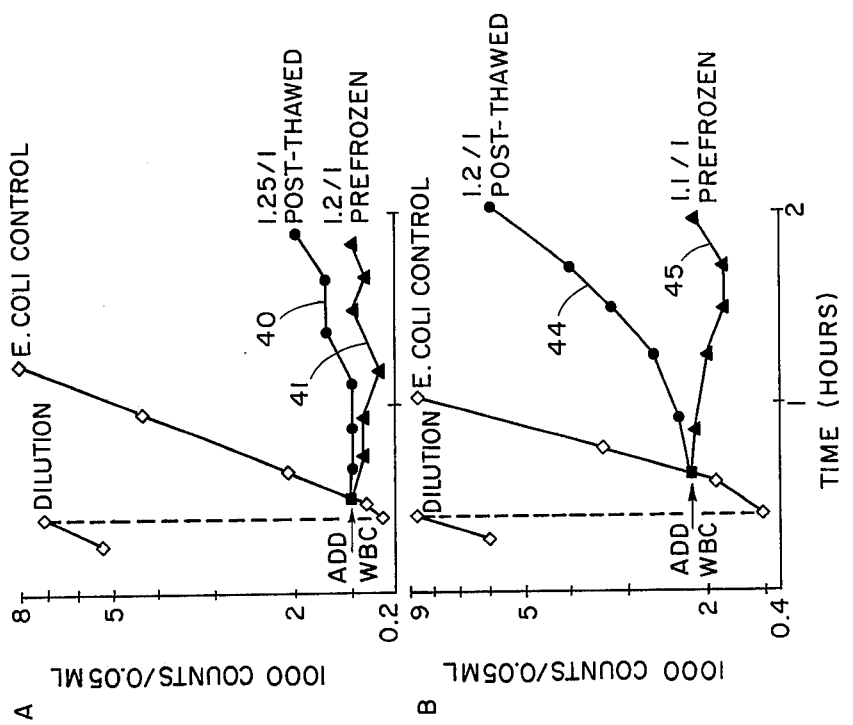
FIG. 6 is a graphical comparison of the inhibition of growth of E. coli by cryopreserved granulocytes.

Application of the growth inhibition test to various samples of frozen white cells clearly demonstrates its ability to distinguish viable postthawed cells from those which had undergone cryoinjury. Growth curves of E. coli exposed to white cells frozen under optimum conditions were compared with those with another aliquot of cells deliberately subject to conditions which produced thawed cells with low myeloperoxidase activity and high trypan blue staining, with the results shown in FIG. 6 which illustrates the inhibition of growth of E. coli by crypreserved granulocytes. Growth curves of E. coli are plotted in the presence of comparable quantities of white cells frozen at different cooling rates. Curves 40 and 41 are for white cells frozen at −2.0° C/min. and show inhibited growth comparable to the unfrozen (prefrozen) sample. Curves 44 and 45 are for white cells from the same unit frozen at 10° C/min. The curves marked "E. coli control" indicate the uninhibited growth rate after dilution. Cells were frozen only with residual HES after sedimentation of buffy coat. The "traumatized" cells were much less able to inhibit the growth of E. coli, curves 40 and 41, than those processed optimally, curves 44 and 45.

There is as yet no entirely satisfactory in vitro test which forecasts in vivo granulocyte function. Like platelets, numerous physiological characteristics can be assessed. Several of such characteristics taken together have been relied on to help evolve a satisfactory method to concentrate and cryopreserve buffy coat granulocytes. To this end, cell size distributions were made to rapidly screen for morphological change during manipulations of white cells. Volume changes and fragmentation are easily assessed this way. Trypan-blue dye exclusion was used to enumerate intactness and cryoplasmic membrane characteristics of thawed graulocytes. Myeloperoxidase was employed as a criterion of cytoplasmic granularity; the thesis being that adequately frozen granulocytes should retain an enzyme function related to the microbicidal phase of phagocytosis. Inhibition of growth of E. coli also was studied as a means to describe the capacity of cryopreserved granulocytes to undergo the ingestion aspect of phagocytosis.

Similar studies have been conducted with buffy coat leukocytes sedimented with dextran or polyvinylpyrrolidone (PVP) and frozen with 10 and 15% DMSO in the presence or absence of 5 and 10% glucose. Freezing rates, storage times, thawing times and temperatures were similar to those described supra. The phagocytic index based on the percentage of neutrophils containing one or more polystyrene granules after 2 minutes of incubation at 37° C was 5–6% for frozen-thawed cells diluted with plasma to 2% DMSO, and 89% with fresh cells. Under these conditions uniformly high eosin exclusion was observed despite varying phagocytosis. Later, phagocytosis was found to increase to 59% on dilution of thawed cells with plasma and to 90% on dilution to 1% DMSO. Thus, an addition of particle ingestion due to DMSO might have occurred. However, after removal or reduction of DMSO these cells gave the same magnitude of phagocytosis as eosin exclusion. In the present experiments, Table 2, there was no effect of DMSO on trypan-blue exclusion in prefrozen cells. Freezing and thawing, however, produced a significant reduction with both HES and HES + DMSO, and washing produced an expected further reduction. Myeloperoxidase related to the countable polymorphonuclear cells recovered after thawing and suggests that most, i.e. 60–70%, of these should be capable of microbicidal activity. This is substantiated in part from the slopes of the growth inhibition studies, FIGS. 5 and 6, wherein the high enzyme cells gave the greatest suppression of growth of E. coli.

The method of the present invention has not shown the magnitude of nuclear change described in the art in several hours of postthaw observation. The difference may be attributable in part to HES or in the manner of manipulation of the granulocytes. Nuclear integrity would, therefore, have an important bearing on post-thawed stability and should be reconciled with observations of cytoplasmic function.

In summary, granulocyte preservation has been undertaken using hydroxyethyl starch for both sedimentation of red cells and cryopreservation of buffy coat white cells from CPD whole blood. Buffy coats were mixed with HES to a final concentration of 4% (w/v) and hemotocrit of from 20% to 30%, and sedimented in inverted plastic syringes. The leukocyte enriched, 100–500X, supernatant was frozen at 2.0° C/min. to −80° C and stored frozen up to three months. Alternatively sedimented leukocytes were frozen after a slow addition of 10% DMSO to 5%. Tubes were thawed at 37° C, and DMSO was removed by dilution with Hank's solution containing CPD and centrifugation. The pellets of granulocytes were resuspended in Normosol.

Buffy coat from 10 units yeilded 60 ± 9.7% of the available whole blood leukocytes, of which 43 ± 14% were recovered after sedimentation in HES. Freezing in DMSO yielded all, 101% of the prefrozen leukocytes. Postthawed viability of granulocytes was estimated morphologically and by their ability to inhibit the rate of growth of E. coli. Complete inhibition was observed at a ratio of one E. coli to one granulocyte. Postthawed granulocytes were characterized by high myeloperoxidase activity and exclusion of trypan blue. Approximately 25% of the total available granulocytes in CPD whole blood were recovered.

There is thus provided a process for isolating, freezing and thawing white cells which makes possible the salvage of these cells from buffy coat of centrifuged whole blood. The separation of major blood components is accomplished in sterile bags, and white cell separation is interfaced with collection methods for other components such as plasma and platelets so as to conserve all major cell types. The present cryomethod for white cells employs a combination of cryoprotective agents, i.e. HES which is extracellular in action and also acts as a sedimenting agent, and DMSO which is intracellular in action. Substantially improved preservation of cellular morphology and functions are achieved over previous cryo-techniques in which single agents are used. The system of the present invention is simpler than leukoadhesion and leukopheresis, requires no sophisticated apparatus or highly trained personnel and is accomplished in much less time. The present system allows for a sterile separation of leukocytes with a minimal number of entries into the sterile collection bag.

Obviously many modifications and variations of the present invention are possible in the light of the above teachings. For example, the method herein presented in relation to the preservation of peripheral blood granulocytes may also be applied in several respects to the preservation of the large number of cells isolated by leukopheresis. In addition, the separation of white cells from centrifuged whole blood can be achieved by sedimentation of buffy coat cells in syringes with HES, followed by freezing of leukocyte suspension in plastic test tubes. This is a simpler but non-sterile technique. Further, other rouleaux-promoting agents can be used in the isolation steps. However, they would have to be removed before the HES + DMSO are added to minimize freezing-thawing damage. A combination of 5% DMSO and 4–8% HES can be used alone as cryoprotectant agents. The volume of leukocyte concentrate frozen can vary from 35–85 ml with similar recoveries and functions. In such instances, the bag should be laid flat in a −80° C freezer instead of being stood up. The thawing should be done in a restraining-type holder that allows a suitable thawing rate.

What is claimed is:

1. A method of salvaging human white blood cells from the buffy coat of centrifuged human whole blood comprising:

isolating and removing by centrifuging the platelet rich plasma and a selected volume of the buffy coat of the topmost red cells from a blood collection bag containing a unit of whole blood;

preparing a 40% weight/volume solution of hydroxyethyl starch in water and further diluting this solution in an isotonic solution of salts containing 148 mequiv per liter each of cations $Na^+$ 140, $K^+$ 5 and $Mg^{2+}$ 3, and anions including chloride 98, acetate 27 and gluconate 23 to dilutions on the order of from 10 to 16% of the 40% weight/volume solution;

obtaining a concentration of 4% hydroxyethyl starch at a hematocrit of 0.30 from said diluted solution by admixing selected volumes of concentrated hydroxyethyl starch and sedimenting out the red cells in the cell mixture;

siphoning off the red cells from said mixture of separated and concentrated cells into a sterile bag for storage;

admixing with the remaining white cells a sterile solution of 10% dimethylsulfoxide in said isotonic solution with said sedimented white cells;

freezing said white cells and storing the frozen white cells in an environment maintained at substantially −80° C;

thawing said concentration of white cells, admixing with said thawed cells a sterile wash solution containing an isotonic solution as defined above but adjusted to a pH of 7.4 containing citrate-phosphate-dextrose in a 10 ml volume;

removing the supernatant layer of substantially 8.0 ml; and resuspending the residue of white cells in said adjusted isotonic solution by gentle agitation.

2. The method defined in claim 1 wherein said step of isolating and removing said buffy coat cells by centrifuging is accomplished at 2500 rpm for substantially 5 min., and said step of thawing is accomplished by immersion of the bag containing the concentration of white cells in a water bath maintained at substantially 37° C while shaking at 160 cycles/min. for a period on the order of from 3 to 5 min.

3. The method of claim 2 and further including determining the effects of freezing and thawing of said white cells on growth by determining the ability of said cells to inhibit the growth of Escherichia coli bacteria.

4. The method of claim 3 wherein the step of determining the ability to inhibit growth includes adding inoculum of Escherichia coli bacteria from an overnight culture thereof to a medium of a tissue culture selected for growing such cells in said isotonic solution of salts having a pH of 7.2; and assaying bacterial growth electronically by means of a multichannel cell-size analyzer.

5. The method of claim 4 wherein said Escherichia coli culture is diluted with 10% of said tissue culture medium in said isotonic solution of salts to a count of 2000 per 0.05 ml and maintained at substantially 37° C while shaking and with counts made periodically until exponential growth is established; and further diluting said Escherichia coli culture solution to a count range of substantially 2000–3000 per 0.05 ml and reincubating said culture until exponential growth is reestablished.

6. The method of claim 5 and further including adding to the proliferating Escherichia coli culture a substantially 0.05 ml volume of said thawed white cells further diluted to 15.0 ml with said Escherichia coli culture solution of salts; and incubating the mixture of Escherichia coli bacteria and thawed white cells diluted with hydroxyethyl starch while shaking at 37° C and withdrawing periodically 0.05 ml aliquots thereof and counting the bacteria therein over a period of from about 4 to 7 hours.

7. A system for salvaging human white cells from human whole blood comprising:

centrifuging whole blood and obtaining a selected volume of the buffy coat of the topmost red cells thereof;

sedimenting said buffy coat red cells with hydroxyethyl starch and dimethylsulfoxide in an isotonic solution of salts;

separating said red cells from said solution and admixing with the remaining white cells a sterile solution of dimethylsulfoxide in said isotonic solution;

freezing said white cells and storing said frozen white cells in an environment maintained at substantially −80° C;

thawing said frozen white cells and washing said thawed white cells in a solution containing an isotonic solution of salts;

removing the supernatant layer of said isotonic solution of salts and white cells; and resuspending the residue of white cells in said adjusted isotonic solution by gentle agitation.

8. The system of claim 7 wherein the concentrations of hydroxyethyl starch and dimethylsulfoxide in said sedimenting step are substantially 4% to 5%, respectively, weight/volume, the concentration of dimethylsulfoxide in said sterile solution is substantially 10%, and said washing solution has a pH of substantially 7.4.

9. The system of claim 8 and further including screening said thawed cells by means of electronic cell sizing to estimate cell damage due to freezing.

10. The system of claim 9 wherein sedimenting with hydroxyethyl starch substantially reduces the population of lymphocyte cells leaving a ratio of substantially 85% granulocyte cells and 15% lymphocyte cells in the white cell population obtained by sedimentation of buffy coat red cells.

* * * * *